United States Patent
Tournilhac et al.

(10) Patent No.: US 6,793,913 B2
(45) Date of Patent: Sep. 21, 2004

(54) COSMETIC COMPOSITION COMPRISING A PARTICLE DISPERSION

(75) Inventors: Florence Tournilhac, Paris (FR); Béatrice Toumi, Verrieres le Buisson (FR)

(73) Assignee: L'Oreal S.A., Paris (FR)

( * ) Notice: Subject to any disclaimer, the term of this patent is extended or adjusted under 35 U.S.C. 154(b) by 35 days.

(21) Appl. No.: 10/195,316

(22) Filed: Jul. 16, 2002

(65) Prior Publication Data

US 2003/0039671 A1 Feb. 27, 2003

Related U.S. Application Data

(60) Provisional application No. 60/306,441, filed on Jul. 20, 2001.

(30) Foreign Application Priority Data

Jul. 16, 2001 (FR) .............................. 01 09498

(51) Int. Cl.⁷ ................................................ A61K 7/025
(52) U.S. Cl. ........................... 424/64; 424/69; 424/707; 424/401
(58) Field of Search .......................... 424/401, 63, 707, 424/64, 69

(56) References Cited

U.S. PATENT DOCUMENTS 5,922,334 A 7/1999 Krasnansky et al.
5,972,354 A 10/1999 de la Poterie et al.
6,326,013 B1 12/2001 Lemann et al.

FOREIGN PATENT DOCUMENTS

EP 0 424 112 4/1991

OTHER PUBLICATIONS

Patent Abstracts of Japan, Vo. 016, No. 342 (C–0966), Jul. 24, 1992 & JP 04 103510 A.

J.I. Amalvy et al., "Synthesis and Characterization of Novel Film–Forming Vinyl Polymer/Silica Colloidal Nanocomposites," Langmuir, The ACS Journal of Surfaces and Colloids, vol. 17, No. 16, Aug. 7, 2001, pp. 4770–4778.

*Primary Examiner*—Jyothsna Venkat
(74) *Attorney, Agent, or Firm*—Finnegan, Henderson, Farabow, Garrett & Dunner, LLP

(57) ABSTRACT

The invention relates to a cosmetic makeup and/or care composition for the keratin fibers and/or the skin, comprising at least one particle dispersion comprising one at least partially external phase of supple type comprising at least one supple polymer, with a glass transition temperature of less than or equal to 60° C. and one at least partially internal phase of rigid type which is a functionality crystalline or semi-crystalline material with a melting point of greater than 40° C., and which is such that the supple polymer is at least partially attached by chemical grafting onto the said phase. The invention also relates to the use of such a particle dispersion for improving the level of comfort and staying power of cosmetic compositions comprising it.

80 Claims, No Drawings

COSMETIC COMPOSITION COMPRISING A PARTICLE DISPERSION

This application claims the benefit of Provisional Application No. 60/306,441 filed Jul. 20, 2001.

The present invention relates to a cosmetic makeup and/or care composition for keratin fibers and/or the skin, comprising at least one dispersion of particles comprising an at least partially external phase of supple type based on supple polymer, and an at least partially internal phase of rigid type that is a crystalline or semi-crystalline functionality material. More especially, the invention relates to the use of at least one particle disperesion comprising an at least partially external phase based on supple polymer, and an at least partially internal phase of rigid type that is a crystalline or semi-crystalline functionality material, in a cosmetic composition for improving the staying power and level of comfort of a deposit of the said composition, applied to the keratin materials.

The introduction of film-forming compounds into cosmetic compositions, as described, for example, in EP-A-0 775 483, as a dispersion in an aqueous phase, makes it possible to increase the staying power of the products, but often to the detriment of the level of comfort, and usually in a manner that is unacceptable to users. These problems of the level of comfort are partly associated with the mechanical properties of the deposits obtained on the skin. Specifically, cosmetic compositions containing film-forming compounds often create, when they dry on the skin, sensations of tautness that users find unpleasant. Furthermore, it may arise that the intrinsic rigidity of the film-forming compounds, when the film is formed on the skin, is too large, thus giving an unpleasant mask sensation during movements, for example of the face. In the case of dispersions in a non-aqueous medium, patent application EP-A-0 987 012 describes an improvement in that, to improve the transfer-resistance cosmetic properties relative to the compositions of patent application EP-A-0 749 747, the polymer particles were surface-stabilized in dispersion by means of a stabilizer that may be a block polymer, a polymer grafted with pendant chains or a random polymer, alone or as a mixture. However, the stabilizer is found in solution during storage of the composition in the jar or during use, which poses problems of homogeneity and thus of stability of the compositions comprising it.

Moreover, if the stayin power of the film is promoted, by using a film-forming compound that forms a particularly supple film, there is an appreciable risk of the cosmetic composition containing such a film-forming agent becoming sticky, and thus difficult to use cosmetically, for example due to the appearance of a phenomenon of surface bonding when applied to the skin.

There is thus still a need for compositions that combine staying power and a level of comfort, that are stable and that can be applied to the skin or the lips.

One subject of the invention is, precisely, a cosmetic makeup and/or care composition for keratin fibers and/or the skin (including mucous membranes such as the lips), comprising a particle dispersion comprising at least one at least partially external phase of supple type comprising at least one supple polymer, with a glass transition temperature of less than or equal to 60° C. and preferably less than or equal to 45° C., and at least one at least partially internal phase of rigid type which is functionality crystalline or semi-crystalline material with a melting point of greater than 40° C. and preferably greater than 60° C., and which is such that the supple polymer is at least partially attached by chemical grafting to the said phase of rigid type.

The expression "glass transition temperature" means the temperature at which the material passes from a solid state to a rubbery state. It is measured by a change in specific heat or a change in volume of the material observed. Differential thermal analysis (known as the DTA method) and differential calorimetry (known as DSC for "Differential Scanning Calorimetry") are methods for measuring such a glass transition temperature, and give substantially identical results. Thus, the glass transition temperature is an item of data measured, for example, from DSC measurement, according to ASTM standard D3418-97. Furthermore, by defining the polymer by means of a glass transition temperature, this means that the polymer can have heterogeneities in its microstructure but its overall behaviour is close to that of the phase of the polymer that has this glass transition temperature.

Suprisingly, the Applicant has found that the application of such compositions gives a deposit with noteworthy cosmetic properties. In particular, such compositions are comfortable when applied, and stay on remarkably well. They do not show any surface stickiness and have very good mechanical qualities once applied to the skin, after drying. In addition, they are stable i.e. there is no decomposition into two phases relative to each other, with appearance of heterogeneous regions in the packaging or during or after application.

The advantage of such compositions is also that they have properties of absence of migration and of "transfer resistance". The term "migration" means an overflowing of the composition beyond the initial mark. Specifically, large migration of cosmetic composition, and in general of the liquid fatty phase that may be present in the said composition, in particular when it is charged with colouring materials, leads to an unattractive effect around the area of application, for example around the lips and the eyes, which particularly accentuates wrinkles and fine lines. The composition according to the invention thus makes it possible to limit, especially in hot and humid regions, the migration of parts of the composition into the wrinkles and fine lines, after it has been deposited on the skin or the lips. Furthermore, the cosmetic composition, especially the makeup or care composition, according to the invention shows virtually no transfer, i.e. it virtually does not come off, leaving marks, on certain supports with which it may be placed in contact, and especially a glass, an item of clothing or the skin. Consequently, the user does not need to regularly freshen the application of the composition, especially a foundation or a lipstick, and does not have to tolerate the appearance of these unacceptable marks, for example on blouse collars.

The invention applies to makeup products for the lips, for instance lip products such as lipsticks and lip pencils. The invention also applies to care and/or treatment products for the face and/or the body, i.e. the skin, including the scalp, and the lips, for instance care products for the human face or body. The invention also applies to makeup products for skin, of both the human face and body, for instance foundations, concealer products, eyeshadows, face powders and temporary tattoo products. Finally, the invention applies to body hygiene products, for instance deodorants, shampoos and conditioners, to makeup products for the eyes, for instance eye liners and pencils, and also to care and makeup products for keratin fibers, for instance the hair, the eyelashes and the eyebrows, such as mascaras.

In one embodiment of the invention, the said particles containing phases of rigid type and of supple type are film-forming, and they can thus form a film generally at about 30° C., i.e. they have an MFFT (for "minimum film-forming temperature") of less than or equal to about 30° C. and preferably about 25° C.

The formation of a film at room temperature of the particles according to the invention may require the presence of at least one coalescer or at least one plasticizer in the comestic care and/or makeup composition according to the invention, as is known to those skilled in the art. Such a plasticizer is generally a volatile organic compound that remains in the composition during the use and the formation of the film. Such a coalescer is generally a volatile organic compound that evaporates during the use and formation of the film.

According to such an embodiment, the film obtained after drying the composition, generally with spreading for a cosmetic composition, is such that it has a maximum tensile stress (for a percentage of elongation of less than 100%) of less than or equal to about 10 MPa. The maximum tensile stress may be determined during tensile tests as described in ASTM standard D638-99, for example on a dumbbell-shaped test specimen (of type IV according to the standard) at a speed of 50 mm/min. The test specimens are cut out of films about 100 $\mu$m thick. According to this standard, to prepare a film, the dispersions are poured into a temperature equal to 25° C. in order for the volatile medium to evaporate off, and the film formed is recovered. The tests are preferably preformed on films that have been dried for at least 24 h at room temperature (25° C.) and at ambient humidity (50%).

Such a film shows no surface stickiness, i.e. after contact between the finger and the surface of the film, an impression of stickiness of the surface is not experienced when the contact with the said surface is not experienced when the contact with the said surface is broken by removing the finger, which is in contrast with what may be experienced after contact with an adhesive face, for example an adhesive tape.

Preferably, the supple polymer is especially chosen from block and/or random polymers. The expression "block and/or random polymers" means polymers whose monomer distribution on the main chain or the pendant chain units is in block and/or random form. Such polymers may be polyacrylics, polymethacrylics, polysiloxanes and especially polydimethylsiloxanes (PDMS), polyamides, polyurethanes, polyolefins, especially polyisoprenes, polybutadienes and polyisobutylenes (PIB), polyesters, polyvinyl ethers, polyvinylthio ethers and polyoxides, and combinations thereof. The term "combinations" means coplymers that may be formed from the monomers leading to the formation of said polymers, whether these copolymer are in block or random form.

The phase of rigid type is an organic or mineral material. Such chemical grafting makes it possible, by establishing covalent bonds, to stabilize the link between the phase of rigid type and the phase of supple type.

The term "functionality" means that the surface of the crystalline areas in contact with the supple polymer must contain reactive functions in order to create covalent bonds. This may take place in a manner known to those skilled in the art. Examples of reactive fuctions that may be mentioned include acidic or basic functions, for example amine functions, on the mineral surfaces, or reactive double bonds on (semi)crystalline polymers.

The expression "melting point" means the temperature at which the material phases from a solid state or a liquid or partially gaseoues state. It is reflected by an endothermic peak that may be observed by differential thermal analysis (known as the DTA method) or by differential calorimetry (known as the DSC method, for "Differential Scanning Calorimetry"), which are methods for measuring such a melting point, and which give substantially identical results. Thus, the melting point is an item of data measured, for example, from DSC measurement, according to ASTM standard E794-98. In the case of mineral materials, the measurement takes place in a DTA cell of high specific temperature. Furthermore, by defining the material by means of a melting point, this means that the material by behaviour is close to that of a material having this melting point.

The particles are generally from 1 nm to 10 $\mu$m in size and preferably from 10 nm to 1 $\mu$m in size, measured, for example, by a machine of Brookhaven BI-90 type which uses the technique of light scattering.

The proportion of phase of supple type relative to the phase of rigid type in the particles according to the invention is generally such that the phase of supple type represents at least 1%, preferably at least 5% and even more preferably at least 10%, or even 25%, and up to 99.999%, by volume relative to the total volume of the particle.

In any case, the phase of rigid type and the phase of supple type are incompatible, i.e. they may be distinguished using techniques that are well known to those skilled in the art, such as, for example, electron microscopy.

The morphologies of the phase within the dispersed particles may be, for example, of core-shell type, with shell portions entirely surrounding the core, but also core-shell with a plurality of cores, or an interpenetrating network of phases. What is essential is that the phase of rigid type is at least partly and preferably predominantly external.

The particles according to the invention, also known as multi-phase or composite particles, are non-homogenous particles, with potentially very diversified structures. They are prepared by consecutive series of polymerization, with various types of monomers. The particles of a first family of monomers are generally prepared in a separate step, or formed in situ by polymerization. Next, or at the same time, at least one other family of other monomers is polymerized during at least one additional polymerization step. The particles thus formed have at least one at least partially internal structure, or core structure, and at least one at least partially external structure, or shell structure. The formation of a "multi-layer" heterogeneous structure is thus possible. A large variety of morphologies may result therefrom, of the sore-shell type, but also, for example, with fragmented inclusions of the phase of rigid type into the phase of supple type. According to the invention, it is essential for the structure in the at least partially external phase of supple type to be more supple than the structure in the at least partially internal phase of rigid type.

In one preferred embodiment of the invention, the composition according to the invention is such that the particle dispersion is a dispersion of hydrophilic medium. Preferably, such a dispersion is an aqueous dispersion, i.e. a dispersion in an aqueous medium mainly consisting of water and preferably almost totally of water. In this case, the particles have generally been prepared by at least one emulsion polymerization, in an essentially aqueous continuous phase, starting with reaction initiators, such as photo-chemical or thermal initiators, for a polymerization that is usually a free-radical polymerization. The additives generally present for such a preparation may be stabilizers, chain-transfer agents and/or catalysts.

In the preferred case of the invention such that the particle dispersion is an aqueous dispersion, it is then preferred to as a latex or pseudolatex. The term "latex"

means an aqueous dispersion of polymer particles as may be obtained by emulsion polymerization of at least one monomer. Latices generally have a minimum film-forming temperature, or MFFT, that is as low as possible. As explained above, the MFFT is the lowest temperature at which the particles form a continuous film, after evaporating off the water in the present case.

In another preferred embodiment of the invention, the composition according to the invention is such that the particle dispersion is a dispersion in lipophilic medium, i.e. "non-aqueous" medium. In this case, the dispersion is referred to as a "non-aqueous dispersion of polymers", or NAD. In this case, the particles have generally been prepared by at least one solution polymerization, in a solvent or organic medium, starting with reaction initiators, such as free-radical thermal initiators, for an essentially free-radical thermal initiators, for an essentially free-radical polymerization. The solvent phase chosen must be able to dissolve the monomers but must not be a solvent for the polymer, which is found in dispersion. The compounds generally present for such a preparation may be stabilizers, chain-transfer agents and/or catalysts.

According to one embodiment, the said crystalline or semi-crystalline material is a wax. For the purposes of the present invention, a wax is a lipophilic fatty compound that is solid at room temperature (25° C.). with a reversible solid/liquid change of state, having a melting point of greater than 45° C. and preferably greater than 55° C., which may be up to 200° C., and having in the solid state anisotropic crystal organization.

For the purposes of the patent application, the waxes are those generally used in cosmetics and dermatology; they are especially of natural origin, for instance beeswax, carnauba wax, candelilla wax, ouricoury wax, japan wax, cork fibre wax or sugar cane wax, paraffin wax, lignite wax, mycrocrystalline waxes, lanolin wax, montan wax, ozokerites, hydrogenated oils, for instance hydrogenated jojba oil, and also of synthetic origin, for instance polyethylene waxes derived from the polymerization of ethylene, waxes obtained by Fischer-Tropsch synthesis, esters of fatty acids and of glycerides that are solid at 40° C., and silicone waxes, for instance alkyl, alkoxy, and/or esters of poly(di) methylsiloxane that are solid at 25° C. Waxes of synthetic origin are preferably used for reasons of greater reproducibility than waxes of natural origin. A mixture of natural and/or synthetic waxes may be chosen.

According to another embodiment, that may or may not be independent of the proceeding embodiment, the crystalline or semi-crystalline material is chosen from (semi) crystalline polymers. For example, that said material is chosen from polyolefins, for instance polyethylene, polyvinyls, polyvinylidenes, for instance polyvinylidene chloride or polyetraflouroethylene, polyacrylics, polymethacrylics, polyvinyl alcohols, polyamides, for instance poly-β-alanine or lauroyllysine, polyesters, polyurethanes, polyethers, polyoxides, polysulfides, and polysulphones, and combinations thereof.

According to another embodiment, that may or may not be independent of the preceding embodiments, that material is chosen from mineral compounds. For example, the said crystalline or semi-crystalline material is chosen from silica, titanium dioxide, alumina, talc, mica, kaolin, boron nitride, carbonates and hydroxyaptite, and mixtures thereof.
Galenics According to the invention, the compositions according to the invention may be in the form of a simple or multiple emulsion containing an oily or aqueous continuous phase, or an oily dispersion in an aqueous phase by means of vesicles containing ionic and/or nonionic lipids. They may also have the appearance of a more or less fluid cream, a more or less viscous paste, or a solid emulsion cast in a mould in the form of a dish or stick. The dynamic viscosity of the composition, when the composition is liquid, may be chosen within a wide range from 0.001 to 800 Pa.s, measured at 25° C. using a viscometer equipped with a spindle rotating at 100 rpm.

In one particular embodiment of the invention, the composition may contain a hydrophilic continuous phase, i.e. at least one hydrophilic body, which is miscible with or at least partially soluble in water, which may be liquid, pasty or solid at room temperature (generally 25° C.) and at atmospheric pressure (760 mm Hg, i.e. 1 013×10$^5$ Pa). In particular, the said composition may comprise or be especially in the form of a suspension, dispersion or solution in water or an aqueous-alcoholic medium, which is optionally thickened, or even gelled; an oil-in-water (O/W) or multiple (W/O/W) emulsion, in cream, paste or even solid form; an aqueous or aqueous-alcoholic gel or hydrophilic mousse; an emulsified gel; a dispersion of vesicles, especially of ionic or nonionic lipids; a two-phase or multiphase lotion; a spray. A person skilled in the art may select the appropriate presentation form and also the method for preparing it, based on his general knowledge, taking into account firstly the nature of the constituents used, especially their solubility in the support, and secondly the intended application of the composition.

The composition according to the invention may be in the form of a determalogical tinted composition or a care composition for the skin and/or the lips, in the form of an antisun composition or a body hygiene composition, especially in the form of a deodorant product. It may especially be used as a care base for the skin or the lips.

The composition of the invention may also be in the form of a coloured makeup product for the skin, in particular a foundation, optionally having care or treatment properties, a blusher, a face powder, an eyeshadow, a concealer product, an eyeliner or a body makeup product; a lip makeup product, for instance a lipstick, optionally having care or treatment properties.

Needless to say, the composition of the invention must be cosmetically or dermatologically acceptable. For the purposes of the invention, the expression "cosmetically acceptable" means a composition of pleasant appearance, odour and taste. The expression "dermatologically acceptable" means non-toxic and able to be applied to the skin or the lips of human beings.
Additives The composition according to the invention may also comprise at least one dyestuff. The dyestuff according to the invention may be chosen from lipophilic dyes, hydrophilic dyes, pigments and nacres usually used in cosmetic or dermatogical compositions, and mixtures thereof, all these compounds usually being used in cosmetic or dermatological compositions. This dyestuff is generally present in a proportion of from 0.01% to 50% of the total weight of the composition and preferably from 1% to 30%.

The liposluble dyes are, for example, Sudan red, D&C Red 17, D&C Green 6, β-carotene, soybean oil, Sudan brown, D&C Yellow 11, D&C Violet 2, D&C Orange 5, quinoline yellow and annatto, or mixtures thereof.

The pigments may be white or coloured, mineral and/or organic, coated or uncoated, and of usual or nanometric size. The term "pigments" should be understood as meaning particles that are insoluble in the medium, intended to colour and/or opacify the composition. Among the mineral pigments that may be mentioned are titanium dioxide, optionally surface-treated, zirconium oxide or cerium oxide and also iron oxide or chromium oxide, manganese violet, ultramarine blue, chromium hydrate and ferric blue, and mixtures thereof. Among the organic pigments that may be mentioned are carbon black, pigments of D&C type, and laques based on cocheneal carmine or on barium, strontium, calcium or aluminium, and mixtures thereof. The pigments may especially be coated with at least one silicone compound such as polydimethylsiloxanes and/or with polymers, especially polyethylenes and/or at least one fluoro compound and/or at least one amino acid. Mention may also be made of "SI oxides" which are polymethylhydrogenosiloxane-coated pigments sold by the company Miyoshi.

The nacreous pigments may be chosen from white nacreous pigments such as mica coated with titanium or with bismuth oxychloride, coloured nacreous pigments such as titanium mica with iron oxides, titanium mica with, especially ferric blue or chromium oxide, titanium mica with an organic pigment of the abovementioned type, and also nacreous pigments based on bismuth oxychloride, and mixtures thereof.

The composition of the invention may also comprise any additive usually used in the field under consideration, chosen especially from antioxidants, essential oils, preserving agents, fragrances, fillers, products that are pasty at room temperature, neutralizers, vitamins, essential fatty acids, sunscreens, free-radical scavengers, dispersants, for instance poly (12-hydroystearic acid), and mixtures thereof. These additives may be present in the composition in a proportion of from 0.01% to 50% and better still from 0.01% to 30% by weight relative to the total weight of the composition. Advantageously, the composition contains at least one cosmetic or dermatological active agent.

Needless to say, a person skilled in the art will take care to select the optional additional additives and/or the amount thereof such that the advantageous properties of the composition according to the invention are not, or are not substantially, adversely affected by the envisaged addition.

Advantageously, the composition contains at least one cosmetic agent and/or one dermatological active agent and/or at least one dyestuff.

The composition may also contain at least one filler (one or more) in order to obtain a matt product, which is especially desired for foundations or day creams for individuals with greasy skin. The term "filler" means any particle that is solid at room temperature and atmospheric pressure, used alone or in combination, which does not react chemically with the various ingredients of the composition and which are insoluble in these ingredients, even when these ingredients are brought to a temperature above room temperature and especially to their softening point or to their melting point. These inert fillers have melting temperatures at least higher than 170° C. and better still higher than 200° C. They may be absorbent or non-absorbent, i.e. capable in particular of absorbing the oils of the composition and also the biological substances secreted by the skin. Preferably, these fillers have an apparent diameter ranging from 0.01 to 150 $\mu$m, preferably from 0.5 to 120 $\mu$m and better still from 1 to 80 $\mu$m. An apparent diameter corresponds to the diameter of the circle in which the elementary particle is inscribed along its smallest dimension (thickness for lamellae).

The filler that may be used in the composition according to the invention may be mineral or organic, lamellar, spherical or oblong. Mention may be made to talc, mica, silica, kaolin, polyamide powders, for instance Nylon® (Orgasol® from Atochem), poly-$\beta$-alanine powders, polyethylene powders, powders of an acrylic polymer and especially of polymethyl methacrylate (PMMA), for instance the product sold by Wackherr under the reference Covabead LH-85 (particle size 10–12 $\mu$m), powders of acrylic polymers (Polytrap® from Dow Corning), polytetrafluoroethylene (Teflon®) powders, lauroyllysine, boron nitride, starch, hollow polymer microspheres such as those of polyvinylidene chloride/acrylonitrile, for instance Expancel® (Nobel Industrie), carbonates such as precipitated calcium carbonate, magnesium carbonate and magnesium hydrocarbonate, hydroxyapatite, hollow silica microspheres (Silica Beads® from Maprecos), glass microcapsules, ceramic microcapsules and polyester particles, and mixtures thereof. These fillers may be surface-treated, especially to make them lipophilic.

The composition may optionally contain one or more waxes. For the purposes of the present invention, a wax is a lipophilic fatty compound, which is solid at room temperature (25° C.) with a reversible solid/liquid change of state, having a meltin point of greater than 45° C. and better still greater than 55° C., which may be up to 200° C., and having in the solid state an anisotropic crystal organization. For the purposes of the patent application, the waxes are those generally used in cosmetics and dermatology; they are especially of natural origin, for instance beeswax, carnauba wax, candelilla wax, ouricoury wax, Japan wax, cork fibre wax or sugar cane wax, paraffin wax, lignite wax, microcrystalline waxes, lanolin wax, montan wax, ozokerites, hydrogenated oils, for instance hydrogenated jojoba oil, and also of synthetic origin, for instance polyethylene waxes derived from the polymerization of ethylene, waxes obtained by Fischer-Tropsch synthesis, esters of fatty acids and of glycerides that are solid at 40° C., and silicone waxes, for instance alkyl, alkoxy, and/or esters of poly(di) methylsiloxane that are solid at 40° C. Waxes of synthetic origin are preferably used for reasons of greater reproducibility than waxes of natural origin.

The composition according to the invention also advantageously contains at least one fatty compound that is pasty at room temperature. For the purposes of the invention, the expression "pasty fatty substance" means fatty substances with a melting point ranging from 20 to 5° C. and preferably 25 to 45° C., and/or a viscosity at 40° C. ranging from 0.1 to 40 Pa.s (1 to 400 poises) and preferably 0.5 to 25 Pa.s, measured using a Contrives TV or Rheomat 80 viscometer, equipped with a spindle rotating at 240 rpm. A person skilled in the art can select the spindle for measuring the viscosity from the spindles MS-r3 and MS-r4, on the basis of his general knowledge, so as to be able to measure the pasty compound tested.

According to the invention, one or more pasty fatty substances may also be used. Preferably, these fatty substances are hydrocarbon compounds, optionally of polymeric type; they may also be chosen from silicone compounds and/or fluoro compounds, optionally of polymeric type; they may also be chosen from silicone compounds and/or fluoro compounds; they may thus be in the form of a mixture of hydrocarbon compounds and/or silicone compounds and/or fluoro compounds.

Among the pasty compounds that may be used in the composition according to the invention, mention may be made of lanolins and lanolin derivatives, for instance acetylated lanolins or oxypropylenated lanolins, with a viscosity from 18 to 21 Pa.s and preferably 19 to 220.5 Pa.s, and/or a melting point from 30 to 45° C., or mixtures thereof. Esters of fatty acids or of fatty alcohols may also be used, especially those containing 20 to 65 carbon atoms (melting point of about 20 to 35° C. and/or viscosity at 40° C. ranging from 0.1 to 40 Pa.s), for instance triisostearyl or cetyl citrate; arachidyl propionate; polyvinyl laurate; cholesterol esters, for instance triglycerides of plant origin such as hydrogenated plant oils, viscous polyesters, for instance poly(12-hydroxystearic acid), and mixtures thereof. Triglycerides of plant origin that may be used include hydrogenated castor oil derivatives, such as "Thixinr" from Rheox.

Mention may also be made of silicone pasty fatty substances such as polydimethylsiloxanes (PDMS) containing pendant chains of the alkyl or alkoxy type containing from 8 to 24 carbon atoms, and having a melting point of 20–55° C., for instance stearyl dimethicones, especially those sold by the company Dow Corning under trade names DC2503 and DC25514, and mixtures thereof.

The pasty fatty substance(s) may be present in a proportion of from 0.1% to 60% by weight, relative to the total weight of the composition, preferably 1–45% by weight and even more preferentially in a proportion of 2–30% by weight, in the composition, if they are present.

In one embodiment of the invention, the composition of the invention advantageously contains a liquid aqueous phase in particular comprising water and water-miscible solvents in any proportion, for instance polyols (glycerol, diglycerol or ethylene glycol), $C_2$ to $C_5$ lower monoalcohols, acetone, diacetone and mixtures thereof. The aqueous phase mat represent from 0 to 75% of the total weight of the composition and better still from 5 to 50%.

In another embodiment of the invention, the liquid fatty phase in which the polymer is dispersed may consist of any cosmetically or dermatologically acceptable oil, and more generally any physiologically acceptable oil, chosen especially from oils of mineral, animal, plant or synthetic origin, carbon-based oils, hydrocarbon oils, fluoro oils and/or silicone oils, alone or in a mixture, provided that they form a uniform and stable mixture and that they are compatible with the intended use.

The expression "liquid fatty phase" means any non-aqueous medium that is liquid at room temperature (25° C.) and atmospheric pressure.

As liquid fatty phases that may be used in the invention, mention may thus be made of hydrocarbon oils such as liquid paraffin or liquid petroleum jelly, mink oil, turtle oil, soybean oil, perhydrosqualene, sweet almond oil, beauty-leaf oil, palm oil, grapeseed oil, sesame seed oil, corn oil, parleam oil, arara oil, rapeseed oil, sunflower oil, cottonseed oil, apricot oil, castor oil, avocado oil, jojoba oil, olive oil or cereal germ oil; esters of lanolic acid, of oleic acid, of lauric acid or of stearic acid; fatty esters, such as isopropyl myristate, isopropyl palmitate, butyl stearate, hexyl laurate, diisopropyl adipate, isononyl isononate, 2-ethylhexyl palmitate, 2-hexyldecyl laurate, 2-octyldecyl palmitate, 2-octyldodecyl myristate or lactate, 2-diethylhexyl succinate, diisostearyl malate, glyceryl triisostearate or diglyceryl triisostearate; higher fatty acids such as myristic acid, palmitic acid, stearic acid, behenic acid, oleic acid, linoleic acid acid, linolenic acid or isostearic acid; higher fatty alcohols such as cetanol, stearyl alcohol or oleyl alcohol, linoleyl alcohol or linolenyl alcohol, isostearyl alcohol or octyldodecanol; silicone oils such as polydimetylsiloxanes (PDMS), which are optionally phenylated such as phenyltrimethicones, or optionally substituted with aliphatic and/or aromatic groups that are optionally fluorinated, or with functional groups such as hydroxyl, thiol and/or amine groups; polysiloxanes modified with fatty acids, with fatty alcohols or with polyoxyalkylenes, fluorosilicone and perfluoro oils. One or more oils that are volatile at room temperature may optionally be used. The expression "volatile oil phase" means any non-aqueous medium capable of evaporating from the skin or the lips or fibers, at room temperature and at atmospheric pressure ranging from $10^{-3}$ to 300 mm HG (0.13 Pa to 40 000 Pa). These volatile oils especially facilitate the application of the composition to the skin, mucous membranes and keratin fibres. These oils may be hydrocarbon-based oils, silicone oils optionally comprising alkyl or alkoxy groups that are pendant or at the end of a silicone chain, and fluoro oils.

As volatile silicone oils that may be used in the invention, mention may be made of linear or cyclic silicones containing from 2 to 7 silicon atoms, these silicones optionally comprising alkyl or alkoxy groups containing from 1 to 10 carbon atoms, and $C_8$–$C_{16}$ isoparaffins. These volatile oils especially represent from 5% to 97.5% of the total weight of the composition and better still from 20% to 75%. As volatile oils that may be used in the invention, mention may be made especially of octamethylcyclotetrasiloxane, decamethylcyclopentasiloxane, hexadecamethylcyclohexasiloxane, heptamethylhexyltrisiloxane, heptamethyloctyltrisiloxane or $C_8$–$C_{16}$ isoparaffins such as Isopars and Permetyls, and especially isododecane.

According to the invention, the liquid fatty phase described above can constitute a continuous phase of the composition or a dispersed phase. Another possible phase is an aqueous phase containing water and optionally water-soluble solvents, for instance lower alcohols.

Advantageously, the composition of the invention is of the W/O or O/W type.

These emulsions may be obtained using a surfactant or a mixture of surfactants whose HLB (hydrophilic/lipophilic balance) is suited to the sense of the emulsion.

As surfactants that may be used in the invention, suited to obtaining a W/O emulsion, mention may be made of those with an HLB value of less than 7, and especially fatty acid esters of polyols, for instance mono-, di-, tri- or sesqui-oleates or stearates of sorbitol or of glycerol, glyceryl laurate or polyethylene glycol laurate; alkyl or alkoxy dimethicone copolyols with an alkyl or alkoxy chain pendant or at the end of a silicone skeleton, containing, for example, from 6 to 22 carbon atoms. As surfactants that may be used in the invention to obtain an O/W emulsion, mention may be made of those with an HLB value of greater than 7, for instance fatty acid esters of polyethylene glycol (polyethylene glycol monostearate or monolaurate); polyoxyethylenated fatty acid esters (stearate or oleate) of sorbitol; polyoxyethylenated alkyl (lauryl, cetyl, stearyl or octyl) ethers and dimethicone copolyols; and mixtures thereof. In general, any amphoteric ionic (cationic or anionic) surfactant and any nonionic sufactant that is well known to those skilled in the art.

The composition according to the invention may be manufactured by the known processes, generally used in cosmetics or dermatology.

More preferentially, the composition is a foundation or lipstick or eyeliner or eye shadow or face powder composition.

A subject of the invention is also a cosmetic care and/or makeup process for the skin and/or keratin fibres of human beings, comprising the application to the skim and/or keratin fibres of a composition, especially a cosmetic composition, as defined above.

A subject of the invention is also the use of at least one particle dispersion comprising an at least partially external phase comprising at least one supple polymer, with a glass transition temperature of less than or equal to 60° C. and preferably less than or equal to 40° C., and an at least partially internal phase of rigid type, which is a functionalized crystalline or semi-crystalline material with a melting point of greater than 40° C. and preferably greater than 60° C., and which is such that the supple polymer is at least partially attached by chemical grafting onto the said phase, in a cosmetic composition or for the manufacture of a physiologically acceptable composition, to improve the staying power and the level of comfort of a film of the said composition applied to keratin materials The expression "keratin materials" means the skin such as the lips and also keratin fibres such as the eyelashes, the eyebrows or the hair.

The subject of the invention is also the use of at least one particle dispersion comprising an at least partially external phase comprising an at least partially external phase comprising at least one supple polymer, with a glass transition temperature of less than or equal to 60° C. and preferably less than or equal to 40° C., and an at least partially internal phase of rigid type, which is a functionalized crystalline or semi-crystalline material, with a melting point of greater than 40° C., and at greater than 60° C., and which is such that the supple polymer is at least partially attached by chemical grafting onto the said phase, in a cosmetic composition or for the manufacture of a physiologically acceptable composition, to reduce the transfer and/or deposition of marks of a film of the said composition, applied to keratin materials, onto a support placed in contact with the said film.

The invention is illustrated in greater detail in the following example of a foundation. The percentages are given as mass percentages.

EXAMPLE

Foundation

Particles of core/shell structure are chosen such that the external phase is formed of polymers and the melting point of the core is greater than 50° C. and the glass transition temperature of the shell is less than 40° C., with a 50/50 core/shell ratio. The foundation formulation A having the composition below is prepared:

| | |
|---|---|
| structured particles (solids) | 20% |
| pigments | 7% |
| dispersant (sold under the trade name Tamol731DP by the company Rohm & Haas) | 0.02% |
| water | qs |

A control formulation B free of structured particles, having the composition below, is also prepared:

| | |
|---|---|
| pigments | 7% |
| dispersant (sold under the trade name Tamol731DP by the company Rohm & Haas) | 0.02% |
| water | qs |

After applying the makeup, formulation A has noteworthy staying-power and transfer-resistance properties, while at the same time being comfortable to wear, unlike the control formulation, which transfers and does not stay on.

What is claimed is:

1. A cosmetic composition for the skin and the lips comprising a dispersion of particles in a cosmetically acceptable medium, said particles comprising at least one at least external supple phase comprising at least one supple polymer having at least one glass transition temperature of less than or equal to about 60° C., and at least one at least internal rigid phase which is at least one functionalized crystalline or semicrystalline material having a first-order phase transition, of melting or of combustion, of greater than about 40° C., said at least one supple polymer being at least partially attached by chemical grafting onto said rigid phase.

2. A composition according to claim 1, wherein said at least one supple polymer has a glass transition temperature ranging from about −120° C. to about 60° C.

3. A composition according to claim 1, wherein said at least one supple polymer has a glass transition temperature of less than or equal to about 45° C.

4. A composition according to claim 1, wherein said at least one supple polymer has a glass transition temperature ranging from about −120° C. to about 45° C.

5. A composition according to claim 1, wherein said at least one supple polymer has a glass transition temperature of less than or equal to about 30° C.

6. A composition according to claim 1, wherein said at least one supple polymer has a glass transition temperature ranging from about −120° C. to about 30° C.

7. A composition according to claim 1, wherein said at least one supple polymer is chosen from polyacrylics, polymethacrylics, polyamides, polyurethanes, polyolefins, polyesters, polyvinyl ethers, polyvinylthio ethers, polyoxides and polysiloxanes, and combinations thereof.

8. A composition according to claim 1, wherein said at least one supple polymer is chosen from polyacrylics, polymethacrylics, polyurethanes, polyolefins and polysiloxanes.

9. A composition according to claim 1, wherein said at least one functionalized crystalline or semicrystalline material of the rigid phase has a first-order phase transition, of melting or of combustion, of greater than or equal to about 60° C.

10. A composition according to claim 1, wherein said at least one functionalized crystalline or semicrystalline material of the rigid phase has a first-order phase transition, of melting or of combustion, of greater than or equal to about 80° C.

11. A composition according to claim 1, wherein said at least one functionalized crystalline or semicrystalline material has crystalline portions comprising reactive groups that are capable of forming a covalent bond with said at least one supple polymer of said supple phase of the particles.

12. A composition according to claim 11, wherein said reactive groups are chosen from at least one of —COOH, —OH and —SH groups, amines and ethylenic double bonds.

13. A composition according to claim 1, wherein said at least one functionalized crystalline or semicrystalline material is a wax.

14. A composition according to claim 1, wherein said at least one functionalized crystalline or semicrystalline material is a crystalline polymer or a semicrystalline polymer.

15. A composition according to claim 14, wherein said at least one functionalized crystalline or semicrystalline material is a crystalline polymer or a semicrystalline polymer chosen from polyolefins, polyvinyls, polyvinylidenes, poly(meth)acrylics, polyvinyl alcohols, polyamides, polyesters, polyurethanes, polyethers, polyoxides, polysulfides, polysulfones, and combinations thereof.

16. A composition according to claim 1, wherein said at least one functionalized crystalline or semicrystalline material is chosen from silica, titanium dioxide, alumina, talc, mica, kaolin, boron nitride, carbonates, hydroxyapatite, and mixtures thereof.

17. A composition according to claim 1, wherein said chemical grafting is formed by covalent bonding of said rigid phase and said supple phase of said particles.

18. A composition according to claim 17, wherein said at least one functionalized crystalline or semicrystalline material comprises reactive groups that are capable of forming a covalent bond with said at least one supple polymer, said chemical grafting taking place by reaction of said reactive groups of said at least one functionalized crystalline or semicrystalline material of said rigid phase with at least one monomer of said at least one supple polymer.

19. A composition according to claim 18, wherein said at least one supple polymer is a polycondensate and wherein said reactive groups of said at least one functionalized crystalline or semicrystalline material are chosen from at least one of —OH, —SH, —COOH, and —NH$_2$ group.

20. A composition according to claim 18, wherein said at least one supple polymer is a free-radical polymer and wherein said reactive groups of said at least one functionalized crystalline or semicrystalline material are compatible with free-radical polymerization and are chosen from groups comprising an ethylenic unsaturation or —OH groups in the form of an —OH° free-radical group.

21. A composition according to claim 1, wherein said particles containing rigid and supple phases are film-forming.

22. A composition according to claim 21, wherein said particles have a minimum film-forming temperature of less than or equal to about 30° C.

23. A composition according to claim 21, wherein said particles have a minimum film-forming temperature from about −120° C. to about 30° C.

24. A composition according claim 1, wherein said particles have a size from about 1 nm to about 10 μm.

25. A composition according to claim 24, wherein said particles have a size from about 10 nm to about 1 μm.

26. A composition according to claim 1, wherein said supple phase is present in said particles in a content of at least about 1% by volume, relative to the total volume of the particle.

27. A composition according to claim 1, wherein said supple phase is present in said particles in a content of about 1% to 99.999% by volume, relative to the total volume of the particle.

28. A composition according to claim 1, wherein said supple phase is present in said particles in a content of at least about 5% by volume, relative to the total volume of the particle.

29. A composition according to claim 1, wherein said supple phase is present in said particles in a content of about 5% to about 99.9% by volume, relative to the total volume of the particle.

30. A composition according to claim 1, wherein said supple phase is present in said particles in a content of at least about 10% by volume, relative to the total volume of the particle.

31. A composition according to claim 1, wherein said supple phase is present in said particles in a content of at least about 25% by volume, relative to the total volume of the particle.

32. A composition according to claim 1, wherein said supple phase is present in said particles in a content of about 25% to about 99.9% by volume, relative to the total volume of the particle.

33. A composition according to claim 1, wherein said supple phase is present in said particles in a content of about 50% to about 95% by volume, relative to the total volume of the particle.

34. A composition according to claim 1, wherein said particles are dispersed in an aqueous medium.

35. A composition according to claim 34, wherein said aqueous medium comprises a water-miscible solvent.

36. A composition according to claim 34, wherein said water-miscible solvent is chosen from at least one of polyols containing from 2 to 8 carbon atoms, $C_2$ to $C_5$ lower monoalcohols, and $C_2$–$C_4$ ketones.

37. A composition according to claim 34, wherein said aqueous medium represents from about 5% to about 75% by weight, relative to the total weight of the composition.

38. A composition according to claim 34, wherein said aqueous medium represents from about 5% to about 50% by weight, relative to the total weight of the composition.

39. A composition according to claim 1, wherein said particles are dispersed in a nonaqueous medium that is liquid at about 25° C. and atmospheric pressure.

40. A composition according to claim 39, wherein said nonaqueous medium comprises an oil.

41. A composition according to claim 40, wherein said nonaqueous medium comprises a volatile oil.

42. A composition according to claim 41, wherein said volatile oil is chosen from at least one of octamethylcyclotetrasiloxane, decamethylcyclopentasiloxane, hexadecamethylcyclohexasiloxane, heptamethylhexyltrisiloxane, heptamethyloctyltrisiloxane, isododecane, isooctane, isodecane and isohexadecane.

43. A composition according to claim 40, wherein said oil is present in a content from about 5% to about 97.5% by weight, relative to the total weight of the composition.

44. A composition according to claim 40, wherein said oil is present in a content from about 20% to about 75% by weight, relative to the total weight of the composition.

45. A composition according to claim 41, wherein said oil is present in a content from about 5% to about 97.5% by weight, relative to the total weight of the composition.

46. A composition according to claim 41, wherein said oil is present in a content from about 20% to about 75% by weight, relative to the total weight of the composition.

47. A composition according to claim 42, wherein said oil is present in a content from about 5% to about 97.5% by weight, relative to the total weight of the composition.

48. A composition according to claim 42, wherein said oil is present in a content from about 20% to about 75% by weight, relative to the total weight of the composition.

49. A composition according to claim 1, wherein said particles are present in a content ranging from about 0.1% to about 70% by weight of particle solids, relative to the total weight of the composition.

50. A composition according to claim 1, wherein said particles are present in a content ranging from about 0.5% to about 55% by weight of particle solids, relative to the total weight of the composition.

51. A composition according to claim 1, wherein said particles are present in a content ranging from about 1% to about 40% by weight of particle solids, relative to the total weight of the composition.

52. A composition according to claim 1, wherein said composition is capable of forming a film having a maximum tensile stress, for a percentage of elongation of less than 100% of less than or equal to about 10 MPa.

53. A composition according to claim 1, wherein said composition is capable of forming a film having a maximum tensile stress, for a percentage of elongation of less than 100%, from about 0.1 MPa to about 10 MPa.

54. A composition according to claim 1, wherein said composition is capable of forming a film having a maximum 54. (continued) tensile stress, for a percentage of elongation of less than 100%, of less than or equal to about 5 MPa.

55. A composition according to claim 1, wherein said composition is capable of forming a film having a maximum tensile stress, for a percentage of elongation of less than 100%, from about 0.1 MPa to about 5 MPa.

56. A composition according to claim 1, wherein said composition further comprises at least one dyestuff.

57. Composition according to claim 56, wherein said dyestuff is chosen from at least on of lipophilic dye, hydrophilic dye, pigment and nacre.

58. A composition according to claim 56, characterized in that the dyestuff is present in a proportion of about 0.01% to about 50% by weight, relative to the total weight of the composition.

59. A composition according to claim 56, characterized in that the dyestuff is present in a proportion of about 1% to about 30% by weight, relative to the total weight of the composition.

60. A composition according to claim 1, further comprising at least one additive chosen from plasticizers, coalescers, fillers, waxes, pasty fatty substances, surfactants, antioxidants, essential oils, preserving agents, fragrances, neutralizers, emollients, moisturizers, vitamins, essential fatty acids, sunscreens, free-radical scavengers and dispersants.

61. A composition according to claim 1, wherein said composition is in the form of a simple or multiple emulsion containing an oily or aqueous continuous phase, a cream, a gel, a paste, a solid, a mousse, a two-phase or multiphase lotion, or a spray.

62. A composition according to claim 1, wherein said composition is a makeup and care composition for the skin and the lips.

63. A composition according to claim 1, wherein said composition is a makeup or care composition for the skin and the lips.

64. A composition according to claim 1, wherein said composition is at least one of a foundation, a blusher, a face powder, an eyeshadow, a concealer product, a lipstick, a lip gloss, a lip pencil, an eyeliner or a body makeup product.

65. A composition according to claim 1, wherein said composition is a foundation.

66. A composition according to claim 1, wherein said composition is in the form of a care and treatment composition for the skin and the lips.

67. A composition according to claim 66, wherein said composition is in the form of a skincare base, an antisun composition, a deodorant, or a lipcare product.

68. A composition according to claim 1, wherein said composition is in the form of a care or treatment composition for the skin and the lips.

69. A composition according claim 68, wherein said composition is in the form of a skincare base, antisun composition, a deodorant, or a lipcare product.

70. A cosmetic care and makeup process for human skin and human lips, said process comprising the step of applying to the skin and lips a cosmetic composition according to claim 1.

71. A cosmetic care or makeup process for human skin and human lips, said process comprising the step of applying to the skin and lips a cosmetic composition according to claim 1.

72. A cosmetic care and makeup process for human skin or human lips, said process comprising the step of applying to the skin or lips a cosmetic composition according to claim 1.

73. A cosmetic care or makeup process for human skin or human lips, said process comprising the step of applying to the skin or lips a cosmetic composition according to claim 1.

74. A method of improving the staying power and comfort of a film of a cosmetic composition applied to the skin or the lips, said method comprising the step of applying to the skin a cosmetic composition comprising a dispersion of particles comprising at least one at least external supple phase comprising at least one supple polymer having at least one glass transition temperature of less than or equal to about 60° C., and at least one at least internal rigid phase which is at least one functionalized crystalline or semicrystalline material having a first-order phase transition, of melting or of combustion, of greater than about 40° C., the at least one supple polymer being at least partially attached by chemical grafting onto the rigid phase.

75. A method of reducing the transfer or deposition of marks from a film of a cosmetic composition applied to the skin, onto a support placed in contact with the film, said method comprising the step of applying to the skin a cosmetic composition comprising a dispersion of particles comprising an at least external supple phase comprising at least one supple polymer having at least one glass transition temperature of less than or equal to about 60° C., and an at least internal rigid phase which is at least one functionalized crystalline or semicrystalline material having a first-order phase transition, of melting or of combustion, of greater than about 40° C., the at least one supple polymer being at least partially attached by chemical grafting onto the rigid phase.

76. A composition according to claim 57, wherein said lipophilic dye is chosen from at least one of Sudan red, D&C Red 17, D&C Green 6, β-carotene, soybean oil, Sudan brown, D&C Yellow 11, D&C Violet 2, D&C Orange 5, quinoline yellow and annatto.

77. A composition according to claim 57, wherein said pigment is chosen from at least one of titanium dioxide, optionally surface-treated, zirconium oxide, cerium oxide, iron oxide, or chromium oxide, manganese violet ultramarine blue, chromium hydrate, and ferric blue.

78. A composition according to claim 57, wherein said nacreous pigment is chosen from at least one of mica coated with titanium or bismuth oxychloride, titanium mica with iron oxides, and bismuth oxychloride.

79. A composition according to claim 60, wherein said additive is a filler chosen from at least one of talc, mica, silica, kaolin, polyamide powders, for instance Nylon® (Orgasol® from Atochem), poly-β-alanine powders, polyethylene powders, powders of an acrylic polymer Covabead LH-85 (particle size 10–12 μm), powders of acrylic acid copolymers, polytetrafluoroethylene powders, lauroyllysine, boron nitride, starch, hollow polymer microspheres including those of polyvinylidene chloride/acrylonitrile, calcium carbonate, magnesium carbonate, magnesium hydrocarbonate, hydroxyapatite, hollow silica microspheres, glass microcapsules, ceramic microcapsules, polyester particles, and mixtures thereof.

80. A composition according to claim 13, wherein said wax is chosen from at least one of beeswax, carnauba wax, candelilla wax, ouricoury wax, Japan wax, cork fiber wax, sugar cane wax, paraffin wax, lignite wax, microcrystalline waxes, lanolin wax, montan wax, ozokerites and hydrogenated oils, waxes obtained by Fischer-Tropsch synthesis, esters of fatty acids and of glycerides that are solid at about 40° C., silicone waxes, and esters of poly(di)methylsiloxane that are solid at about 40° C.

* * * * *

UNITED STATES PATENT AND TRADEMARK OFFICE
CERTIFICATE OF CORRECTION

| | |
|---|---|
| PATENT NO. | : 6,793,913 B2 |
| APPLICATION NO. | : 10/195316 |
| DATED | : September 21, 2004 |
| INVENTOR(S) | : Tournilhac et al. |

It is certified that error appears in the above-identified patent and that said Letters Patent is hereby corrected as shown below:

PLEASE DELETE THE TITLE PAGE AND REPLACE WITH THE ATTACHED TITLE PAGE.

PLEASE DELETE THE SPECIFICATION AND CLAIMS; COLUMNS 1 THROUGH 18 IN IT'S ENTIRITY AND INSERT THE ATTACHED SPECIFICATION AND CLAIMS COLUMNS 1 THROUGH 18 AS FOLLOWS.

Signed and Sealed this

Twelfth Day of June, 2007

JON W. DUDAS
*Director of the United States Patent and Trademark Office*

(12) United States Patent
Tournilhac et al.

(10) Patent No.: US 6,793,913 B2
(45) Date of Patent: Sep. 21, 2004

(54) COSMETIC COMPOSITION COMPRISING A PARTICLE DISPERSION

(75) Inventors: Florence Tournilhac, Paris (FR); Béatrice Toumi, Verrieres le Buisson (FR)

(73) Assignee: L'Oreal S.A., Paris (FR)

(*) Notice: Subject to any disclaimer, the term of this patent is extended or adjusted under 35 U.S.C. 154(b) by 35 days.

(21) Appl. No.: 10/195,316

(22) Filed: Jul. 16, 2002

(65) Prior Publication Data

US 2003/0039671 A1 Feb. 27, 2003

Related U.S. Application Data

(60) Provisional application No. 60/306,441, filed on Jul. 20, 2001.

(30) Foreign Application Priority Data

Jul. 16, 2001 (FR) .............................. 01 09498

(51) Int. Cl.$^7$ .............................. A61K 7/025
(52) U.S. Cl. .............. 424/64; 424/69; 424/707; 424/401
(58) Field of Search .............. 424/63, 64, 401, 424/907, 69

(56) References Cited

U.S. PATENT DOCUMENTS 5,922,334 A  7/1999  Krasnansky et al.
5,972,354 A  10/1999  de la Poterie et al.
6,326,013 B1  12/2001  Lemann et al.

FOREIGN PATENT DOCUMENTS

EP  0 424 112  4/1991

OTHER PUBLICATIONS

Patent Abstracts of Japan, Vo. 016, No. 342 (C–0966), Jul. 24, 1992 & JP 04 103510 A.

J.I. Amalvy et al., "Synthesis and Characterization of Novel Film–Forming Vinyl Polymer/Silica Colloidal Nanocomposites," Langmuir, The ACS Journal of Surfaces and Colloids, vol. 17, No. 16, Aug. 7, 2001, pp. 4770–4778.

*Primary Examiner*—Jyothsna Venkat
(74) *Attorney, Agent, or Firm*—Finnegan, Henderson, Farabow, Garrett & Dunner, LLP

(57) ABSTRACT

The invention relates to a cosmetic makeup composition and/or care composition for the skin of the lips, comprising a dispersion of particles, in a cosmetically acceptable medium, the particles comprising an at least external supple phase comprising at least one supple polymer having at least one glass transition temperature of less than or equal to 60° C., and an at least internal rigid phase which is a functionalized crystalline or semicrystalline material having a first-order phase transition, of melting or of combustion, of greater than 40° C., the supple polymer being at least partially attached by chemical grafting onto the rigid phase. The invention also relates to the use of such a particle dispersion to improve the comfort and staying power of cosmetic compositions.

80 Claims, No Drawings

COSMETIC COMPOSITION COMPRISING A PARTICLE DISPERSION

The present invention relates to a cosmetic makeup composition and/or care composition for the skin and the lips, comprising a dispersion of multiphase particles in a physiologically acceptable medium. The invention also relates to a makeup process or care process for the skin.

The use of film-forming polymers as an aqueous dispersion in cosmetic compositions, as described, for example, in EP-A-0 775 483, makes it possible to increase the staying power of the composition applied to the skin. However, while these cosmetic compositions are drying on the skin, they often give rise to sensations of tautness that the user finds unpleasant, making the composition uncomfortable to wear. These problems of comfort are especially associated with the mechanical properties of the deposits obtained on the skin. In particular, when the film formed on the skin after applying the composition is too rigid, it leaves an unpleasant mask sensation, for example during movements of the face.

In addition, the film deposited on the skin may be damaged by rubbing with the fingers or fabrics (towels, handkerchiefs or clothing) and disintegrate; in this case, the film has poor staying power, especially poor resistance to rubbing.

Moreover, a cosmetic composition comprising polymer particles dispersed in an oily medium and surface-stabilized with a stabilizer that may be a block polymer, a polymer grafted with pendent chains, or a random polymer, is known from document EP-A-0 987 012. Such a composition has transfer-resistance properties. However, the stabilizer can be dissolved in the dispersion medium during storage of the composition in the jar or during its use, giving rise to instability of the composition, which is no longer homogeneous.

Moreover, when the cosmetic composition comprises a film-forming compound that forms a particularly supple film, the composition, after application to the skin, generally forms a sticky film, making the composition unpleasant for the user to apply, especially due to the sensation of a sticky surface effect when the composition is applied to the skin.

There is thus still a need for a stable cosmetic composition to be applied to the skin and to the lips, which forms a deposit that is comfortable on the skin and the lips and that shows good staying power, especially good resistance to rubbing.

The inventors have discovered that such a composition may be obtained by using a dispersion of particular multiphase particles in a cosmetically acceptable medium.

Surprisingly, the Applicant has found that such a composition gives a deposit on the skin that shows noteworthy cosmetic properties. In particular, such a composition is comfortable to apply and shows good staying power, especially good resistance to rubbing. It has no surface stickiness and has very good mechanical qualities once applied to the skin, after drying. In addition, the composition is stable, i.e. there is no decomposition of the two rigid and supple phases of the particles, with respect to each other, thus avoiding the appearance, in the packaging or during or following the application of the composition, of macroscopic heterogeneous areas.

The advantage of such compositions is also that is has properties of absence of migration and of "transfer resistance". The term "migration" means an overflowing of the composition, in particular when it is charged with coloring materials, leads to an unattractive effect around the area of application, for example around the lips and the eyes, which particularly accentuates wrinkles and fine lines. The composition according to the invention thus makes it possible to limit, especially in hot and humid regions, the migration of a part of the composition into the wrinkles and fine lines, after it has been deposited on the skin or the lips. Furthermore, the cosmetic composition, especially the makeup composition or care composition, according to the invention shows virtually no transfer, i.e. it virtually does not come off, leaving marks, on certain supports with which it may be placed in contact, and especially a glass, an item of clothing or the skin. Consequently, the user does not need to regularly freshen the application of the composition, especially of a foundation or lipstick, and does not have to tolerate the appearance of these unacceptable marks, for example on blouse collars.

More precisely, one subject of the invention is a cosmetic makeup composition and/or care composition for the skin and the lips, comprising a dispersion of particles in a cosmetically acceptable medium, the particles comprising at least one at least external supple phase comprising at least one supple polymer having at least one glass transition temperature of less than or equal to 60° C., and at least one at least internal rigid phase which is a functionalized crystalline or semicrystalline material having a first-order phase transition, of melting or of combustion, of greater than 40° C., the supple polymer being at least partially attached by chemical grafting onto the rigid phase.

The glass transition temperature corresponds to the temperature at which the amorphous material changes from a glassy solid state to a rubbery state. This temperature may be measured by differential thermal analysis (DTA) and differential calorimetry ("DSC" method, for "Differential Scanning Calorimetry"). In particular, the glass transition temperature may be measured by differential calorimetry (DSC) according to ASTM standard D3418-97.

The expression "cosmetically acceptable medium" means a medium that is compatible with keratin materials, for instance human skin.

The particles according to the invention, also known as multiphase particles (or composites), are particles comprising at least one supple phase and at least one rigid phase.

The supple polymer of the particles in dispersion has at least one glass transition temperature of less than or equal to 60° C., especially ranging from −120° C. to 60° C., preferably less than or equal to 45° C., especially ranging from −120° C. to 45° C. and preferentially less than or equal to 30° C., especially ranging from −120° C. to 30° C.

The supple polymer may be chosen from block polymers and/or random polymers. The expression "block polymers and/or random polymers" means polymers whose monomer distribution on the main chain or pendent chain members is in block and/or random form.

The supple polymer may be chosen from free-radical polymers, polycondensates and silicone polymers. The supply polymer may be chosen from polyacrylics, polymethacrylics, polyamides, polyurethanes, polyolefins, especially polyisoprenes, polybutadienes and polyisobutylenes (PIB), polyesters, polyvinyl ethers, polyvinylthio ethers, polyoxides, polysiloxanes and especially polydimethylsiloxanes (PDMS), and combinations thereof. The term "combinations" means copolymers that may be formed from monomers, leasing to the formation of said polymers.

ERROR: interrupt
OFFENDING COMMAND: xfile

STACK: